(12) United States Patent
Refai et al.

(10) Patent No.: US 8,182,537 B2
(45) Date of Patent: May 22, 2012

(54) VERTEBRAL BODY REPLACEMENT DEVICE AND METHOD FOR USE TO MAINTAIN A SPACE BETWEEN TWO VERTEBRAL BODIES WITHIN A SPINE

(75) Inventors: Daniel Refai, Saint Louis, MO (US); Jeffrey A. Farris, Berne, IN (US)

(73) Assignee: Aesculap Implant Systems, LLC, Center Valley, PA (US)

( * ) Notice: Subject to any disclaimer, the term of this patent is extended or adjusted under 35 U.S.C. 154(b) by 1239 days.

(21) Appl. No.: 11/928,532

(22) Filed: Oct. 30, 2007

(65) Prior Publication Data

US 2009/0112324 A1  Apr. 30, 2009

(51) Int. Cl.
*A61F 2/44* (2006.01)
(52) U.S. Cl. .................................................. 623/17.16
(58) Field of Classification Search ..... 623/17.11–17.16
See application file for complete search history.

(56) References Cited

U.S. PATENT DOCUMENTS

| | | | |
|---|---|---|---|
| 2,333,033 A | 10/1943 | Mraz | |
| 4,157,715 A | 6/1979 | Westerhoff | |
| 4,289,123 A | 9/1981 | Dunn | |
| 4,386,603 A | 6/1983 | Mayfield | |
| 4,401,112 A | 8/1983 | Rezaian | |
| 4,553,273 A | 11/1985 | Wu | 623/18 |
| 4,554,914 A | 11/1985 | Kapp et al. | |
| 4,599,086 A | 7/1986 | Doty | |
| 4,636,217 A | 1/1987 | Ogilvie et al. | |
| 4,657,550 A | 4/1987 | Daher | 623/17 |
| 4,892,546 A | 1/1990 | Kotz et al. | |
| 4,932,975 A | 6/1990 | Main et al. | 623/17 |
| 5,002,576 A | 3/1991 | Fuhrmann et al. | |
| 5,236,460 A | 8/1993 | Barber | |
| 5,246,458 A | 9/1993 | Graham | 623/17 |
| 5,281,226 A | 1/1994 | Davydov et al. | |

(Continued)

FOREIGN PATENT DOCUMENTS

DE  30 23 942  1/1982

(Continued)

OTHER PUBLICATIONS

PCT Search Report and Written Opinion Dated Feb. 17, 2010. PCT/US2009/060608, 17 Pgs.

(Continued)

*Primary Examiner* — Thomas C. Barrett
*Assistant Examiner* — Sameh Boles
(74) *Attorney, Agent, or Firm* — RatnerPrestia

(57) ABSTRACT

The vertebral body replacement device includes a body member and a central rod member that has two threaded portions and is configured to be operatively associated with the body member. The device also includes a first end member and a second end member with the end members being configured to threadingly engage the threaded portions of the central rod member. The body member and the two end members are further constructed to inhibit rotational movement of the two end members when the device is positioned within a space within a spine as the two end members will engage the adjacent respective vertebral bodies following rotational actuation of the central rod member causing the end members to move in an axial direction relative to the body member, thereby allowing the two end members to apply a force to the two vertebral bodies. A surgical method using the device is also disclosed.

20 Claims, 8 Drawing Sheets

U.S. PATENT DOCUMENTS

| | | | |
|---|---|---|---|
| 5,290,312 A | 3/1994 | Kojimoto et al. | |
| 5,336,223 A | 8/1994 | Rogers | 606/61 |
| 5,344,459 A | 9/1994 | Swartz | |
| 5,405,391 A | 4/1995 | Henderson et al. | |
| 5,413,602 A | 5/1995 | Metz-Stavenhagen | |
| 5,458,641 A | 10/1995 | Jimenez | 623/17 |
| 5,480,442 A | 1/1996 | Bertagnoli | |
| 5,571,190 A | 11/1996 | Ulrich et al. | |
| 5,571,192 A | 11/1996 | Schonhoffer | 623/17 |
| 5,658,335 A | 8/1997 | Allen | 623/17 |
| 5,702,453 A | 12/1997 | Rabbe et al. | 623/17 |
| 5,702,455 A | 12/1997 | Saggar | 623/17 |
| 5,723,013 A | 3/1998 | Jeanson et al. | 623/17 |
| 5,776,197 A | 7/1998 | Rabbe et al. | 623/17 |
| 5,776,198 A | 7/1998 | Rabbe et al. | 623/17 |
| 5,800,547 A | 9/1998 | Schafer et al. | |
| 5,888,223 A | 3/1999 | Bray | |
| 5,916,267 A | 6/1999 | Tienboon | |
| 5,989,290 A | 11/1999 | Biedermann et al. | 623/17 |
| 6,015,436 A | 1/2000 | Schonhoffer | 623/17 |
| 6,045,579 A | 4/2000 | Hochshuler et al. | |
| 6,080,193 A | 6/2000 | Hochshuler et al. | |
| 6,113,605 A | 9/2000 | Storer | |
| 6,126,660 A | 10/2000 | Dietz | 606/61 |
| 6,126,674 A | 10/2000 | Janzen | |
| 6,129,763 A | 10/2000 | Chauvin et al. | 623/17 |
| 6,159,215 A | 12/2000 | Urbahns et al. | |
| 6,176,881 B1 | 1/2001 | Schar et al. | 623/17.11 |
| 6,190,413 B1 | 2/2001 | Sutcliffe | 623/17.11 |
| 6,190,414 B1 | 2/2001 | Young et al. | |
| 6,193,755 B1 | 2/2001 | Metz-Stavenhagen et al. | 623/17.11 |
| 6,193,756 B1 * | 2/2001 | Studer et al. | 623/17.15 |
| 6,200,348 B1 | 3/2001 | Biedermann et al. | 623/17.11 |
| 6,214,050 B1 | 4/2001 | Huene | 623/17.15 |
| 6,296,665 B1 | 10/2001 | Strnad et al. | |
| 6,299,644 B1 | 10/2001 | Vanderschot | |
| 6,344,057 B1 | 2/2002 | Rabbe et al. | 623/17 |
| 6,352,556 B1 | 3/2002 | Kretschmer et al. | 623/17.11 |
| 6,375,682 B1 | 4/2002 | Fleischmann et al. | 623/17.12 |
| 6,375,683 B1 | 4/2002 | Crozet et al. | 623/17.15 |
| 6,395,032 B1 | 5/2002 | Gauchet | |
| 6,395,034 B1 | 5/2002 | Suddaby | |
| 6,454,806 B1 | 9/2002 | Cohen et al. | 623/17.15 |
| 6,478,800 B1 | 11/2002 | Fraser et al. | |
| 6,524,341 B2 | 2/2003 | Lang et al. | 623/17.15 |
| 6,562,074 B2 | 5/2003 | Gerbec et al. | |
| 6,610,090 B1 | 8/2003 | Bohm et al. | 623/17.11 |
| 6,616,695 B1 | 9/2003 | Crozet et al. | 623/17.11 |
| 6,648,917 B2 | 11/2003 | Gerbec et al. | 623/17.11 |
| 6,660,038 B2 | 12/2003 | Boyer, II et al. | |
| 6,699,246 B2 | 3/2004 | Zucherman | |
| 6,719,796 B2 | 4/2004 | Cohen et al. | |
| 6,723,126 B1 | 4/2004 | Berry | 623/17.11 |
| 6,730,088 B2 | 5/2004 | Yeh | 606/61 |
| 6,752,832 B2 | 6/2004 | Neumann | |
| 6,783,547 B2 | 8/2004 | Castro | |
| 6,808,538 B2 | 10/2004 | Paponneau | 623/17.16 |
| 6,821,298 B1 | 11/2004 | Jackson | 623/17.15 |
| 6,835,206 B2 | 12/2004 | Jackson | 623/17.11 |
| 6,835,207 B2 | 12/2004 | Zacouto | |
| 6,852,129 B2 | 2/2005 | Gerbec et al. | 623/17.15 |
| 6,863,673 B2 | 3/2005 | Gerbec et al. | 606/99 |
| 6,866,682 B1 | 3/2005 | An et al. | 623/17.15 |
| 6,902,579 B2 | 6/2005 | Harms et al. | 623/17.11 |
| 6,908,485 B2 | 6/2005 | Crozet et al. | 623/17.16 |
| 6,953,477 B2 | 10/2005 | Berry | 623/17.11 |
| 6,981,989 B1 | 1/2006 | Fleischmann | |
| 7,022,138 B2 | 4/2006 | Mashburn | 623/17.13 |
| 7,029,498 B2 | 4/2006 | Boehm et al. | 623/17.11 |
| 7,056,343 B2 | 6/2006 | Schafer et al. | 623/17.11 |
| 7,156,874 B2 | 1/2007 | Paponneau et al. | |
| 7,252,673 B2 | 8/2007 | Lim | |
| 7,338,526 B2 | 3/2008 | Steinberg | |
| 7,384,431 B2 | 6/2008 | Berry | |
| 7,575,601 B2 | 8/2009 | Dickson | |
| 7,621,953 B2 | 11/2009 | Braddock et al. | |
| 2001/0005796 A1 | 6/2001 | Zdeblick et al. | |
| 2002/0068978 A1 | 6/2002 | Camino et al. | |
| 2002/0082695 A1 | 6/2002 | Neumann | |
| 2002/0099443 A1 | 7/2002 | Messerli et al. | |
| 2002/0161441 A1 | 10/2002 | Lang et al. | |
| 2003/0045877 A1 | 3/2003 | Yeh | |
| 2003/0191531 A1 | 10/2003 | Berry et al. | |
| 2004/0049271 A1 | 3/2004 | Biedermann et al. | |
| 2004/0059271 A1 | 3/2004 | Berry | |
| 2004/0093083 A1 | 5/2004 | Branch et al. | |
| 2004/0133280 A1 | 7/2004 | Trieu | |
| 2004/0153160 A1 | 8/2004 | Carrasco | |
| 2004/0172129 A1 | 9/2004 | Schafer et al. | |
| 2004/0181283 A1 | 9/2004 | Boyer, II et al. | |
| 2004/0186569 A1 | 9/2004 | Berry | 623/17.11 |
| 2004/0186576 A1 | 9/2004 | Biscup | |
| 2004/0210312 A1 | 10/2004 | Neumann | |
| 2005/0004572 A1 | 1/2005 | Biedermann et al. | |
| 2005/0060036 A1 | 3/2005 | Schultz | |
| 2005/0085910 A1 | 4/2005 | Sweeney | 623/17.11 |
| 2005/0090898 A1 | 4/2005 | Berry et al. | |
| 2005/0113921 A1 | 5/2005 | An et al. | 623/17.11 |
| 2005/0143749 A1 | 6/2005 | Zalenski et al. | |
| 2005/0159814 A1 | 7/2005 | Karahalios | |
| 2005/0187634 A1 | 8/2005 | Berry | 623/17.15 |
| 2005/0234550 A1 | 10/2005 | Metz-Stavenhagen | 623/17.11 |
| 2006/0004447 A1 | 1/2006 | Mastrorio et al. | 623/17.11 |
| 2006/0058877 A1 | 3/2006 | Gutlin et al. | 623/17.11 |
| 2006/0058879 A1 | 3/2006 | Metz-Stavenhagen | 623/17.15 |
| 2006/0074488 A1 | 4/2006 | Abdou | |
| 2006/0074490 A1 | 4/2006 | Sweeney | 623/17.15 |
| 2006/0085073 A1 | 4/2006 | Raiszadeh | |
| 2006/0100710 A1 | 5/2006 | Gutlin et al. | 623/17.15 |
| 2006/0142859 A1 | 6/2006 | McLuen | 623/17.11 |
| 2006/0149371 A1 | 7/2006 | Marik | |
| 2006/0200244 A1 | 9/2006 | Assaker | |
| 2006/0224241 A1 | 10/2006 | Butler et al. | 623/17.15 |
| 2006/0235521 A1 | 10/2006 | Zucherman | |
| 2006/0241762 A1 | 10/2006 | Kraus | 623/17.11 |
| 2006/0241770 A1 | 10/2006 | Rhoda et al. | |
| 2006/0293755 A1 | 12/2006 | Lindner et al. | |
| 2007/0093901 A1 | 4/2007 | Grotz | |
| 2007/0129805 A1 | 6/2007 | Braddock | |
| 2007/0173855 A1 | 7/2007 | Winn | |
| 2007/0191954 A1 | 8/2007 | Hansell et al. | |
| 2007/0203490 A1 | 8/2007 | Zucherman | |
| 2007/0233254 A1 | 10/2007 | Grotz et al. | |
| 2007/0250171 A1 | 10/2007 | Bonin, Jr. | |
| 2007/0255407 A1 * | 11/2007 | Castleman et al. | 623/17.11 |
| 2007/0255408 A1 | 11/2007 | Castleman et al. | |
| 2007/0255410 A1 | 11/2007 | Dickerson et al. | |
| 2007/0255413 A1 | 11/2007 | Edie | |
| 2007/0255421 A1 | 11/2007 | Dickson | |
| 2008/0004705 A1 | 1/2008 | Rogeau et al. | |
| 2008/0021555 A1 | 1/2008 | White | |
| 2008/0021556 A1 | 1/2008 | Edie | |
| 2008/0051896 A1 | 2/2008 | Suddaby | |
| 2008/0058931 A1 | 3/2008 | White | |
| 2008/0140207 A1 | 6/2008 | Olmos | |
| 2008/0154305 A1 | 6/2008 | Foley | |
| 2008/0167726 A1 | 7/2008 | Melkent | |
| 2008/0243254 A1 | 10/2008 | Butler | |
| 2008/0287957 A1 | 11/2008 | Hester et al. | |
| 2008/0288073 A1 | 11/2008 | Renganath et al. | |
| 2009/0076610 A1 | 3/2009 | Afzai | |
| 2009/0105832 A1 | 4/2009 | Allain et al. | |
| 2009/0112324 A1 | 4/2009 | Refai et al. | |
| 2009/0112325 A1 | 4/2009 | Refai et al. | |
| 2009/0216331 A1 | 8/2009 | Grotz | |

FOREIGN PATENT DOCUMENTS

| | | |
|---|---|---|
| DE | 37 29 600 | 3/1989 |
| DE | 40 12 622 | 7/1991 |
| DE | 41 09 941 | 10/1992 |
| DE | 44 09 392 | 3/1994 |
| DE | 4409392 A1 | 9/1995 |
| DE | 44 23 257 | 1/1996 |
| DE | 19 500 170 | 2/1996 |
| DE | 19 509 317 | 9/1996 |

| | | |
|---|---|---|
| DE | 19 519 101 | 11/1996 |
| DE | 196 22 827 | 12/1997 |
| DE | 296 16 778 | 3/1998 |
| DE | 91 07 494 | 10/1998 |
| DE | 198 04 765 | 8/1999 |
| DE | 202 130 13 | 1/2003 |
| DE | 10 357 926 | 9/2005 |
| DE | 203 20 974 | 2/2007 |
| DE | 20 2008 001 261 | 4/2008 |
| EP | 0 188 954 | 7/1986 |
| EP | 0 290 767 | 11/1988 |
| EP | 0 490 159 | 6/1992 |
| EP | 0 567 424 | 10/1993 |
| EP | 0 832 622 | 4/1998 |
| EP | 0 968 692 | 1/2000 |
| EP | 1 080 703 | 3/2001 |
| EP | 1 188 424 | 3/2002 |
| EP | 1 219 266 | 3/2002 |
| EP | 1 459 710 | 9/2004 |
| EP | 1459710 A | 9/2004 |
| EP | 1491165 A | 12/2004 |
| EP | 1 86 7304 | 9/2007 |
| FR | 2 916 956 | 12/2008 |
| JP | 62 164458 | 7/1997 |
| SU | 1 560 184 | 4/1990 |
| SU | 1 739 989 | 6/1992 |
| WO | WO 92 01428 | 2/1992 |
| WO | WO 94 18913 | 9/1994 |
| WO | WO 95 25486 | 9/1995 |
| WO | WO 9525486 | 9/1995 |
| WO | WO 96 17564 | 6/1996 |
| WO | WO 96 37170 | 11/1996 |
| WO | WO 97 47258 | 12/1997 |
| WO | WO 98 46173 | 10/1998 |
| WO | WO 99 39665 | 8/1999 |
| WO | WO 9956675 | 11/1999 |
| WO | WO 9963913 | 12/1999 |
| WO | WO 00 23013 | 4/2000 |
| WO | WO 03 096937 | 11/2003 |
| WO | WO 2004 019827 | 3/2004 |
| WO | WO 2004 026157 | 4/2004 |
| WO | 2004052245 A | 6/2004 |
| WO | WO 2004 093751 | 11/2004 |
| WO | WO 2004 096103 | 11/2004 |
| WO | WO 2004 100837 | 11/2004 |
| WO | WO 2005 055887 | 6/2005 |
| WO | WO 2006 065910 | 6/2006 |
| WO | WO 2007 076261 | 7/2007 |
| WO | WO 2008/065450 | 6/2008 |
| WO | WO 2008/099277 | 8/2008 |
| WO | WO 2009/058576 | 5/2009 |

OTHER PUBLICATIONS

PCT Search Report and Written Opinion Dated Completed Feb. 9, 2009. PCT/US2008/080127, 17 Pgs.

Refai et al., PCT Search Report and Written Opinion dated Feb. 24, 2009, PCT/US2008/080143, 12 pages.

Search Report and Written Opinion for International Application PCT/US2010/022805, Dated Jun. 24, 2010.

U.S. Patent and Trademark Office Non-Final Office Action Dated Dec. 7, 2010, Issued for U.S. Appl. No. 11/928,553.

Final Office Action dated Mar. 17, 2011 for U.S. Appl. No. 11/928,553.

* cited by examiner

VERTEBRAL BODY REPLACEMENT DEVICE AND METHOD FOR USE TO MAINTAIN A SPACE BETWEEN TWO VERTEBRAL BODIES WITHIN A SPINE

CROSS-REFERENCE TO RELATED APPLICATIONS/PATENTS

This application is related to concurrently filed and commonly owned U.S. Non-Provisional patent application Ser. No. 11/928,553, entitled "FOOTPLATE MEMBER AND A METHOD FOR USE IN A VERTEBRAL BODY REPLACEMENT DEVICE" by REFAI et al.

TECHNICAL FIELD

The present invention relates generally to orthopaedic and neurosurgical implants used for insertion within the spine, and more specifically, but not exclusively, concerns devices implanted within the spinal column to replace a resected, fractured or diseased vertebral body and to maintain or reestablish proper spacing between the remaining adjacent vertebral bodies.

BACKGROUND OF THE INVENTION

Damage or disease that affects the integral structure of a vertebral body within an individual's spinal column may lead to neurologic impairment with possible permanent damage to the spinal cord as well as improper neck and back alignment. Maintaining anatomic spacing within the spinal column is critical to ensuring continued functionality of the spinal cord and nerve roots and avoidance of long term serious neurological impairment.

Typically, spinal implants that are used as a spacer type of device have a fixed overall length and are implanted without the ability to adjust the degree of expansion or curvature. Recent developments of spinal spacers have resulted in devices that may be lengthened in vivo by rotary motion to match the space presented by the missing vertebral body. Problems that have been seen with these types of designs include post-placement migration attributable to the torsional forces applied to the implant during the lengthening process risking the patient to neurologic injury, the improper sizing of the implant relative to the presented clinical space, limited device access ports for height manipulation, and the lack of endplate angulation possibilities.

SUMMARY OF THE INVENTION

Advancement of the state of spinal implants and the surgical management relating to the clinical presentation of missing or damaged vertebral bodies within an intact spinal column is believed desirable. The present invention satisfies the need for improvements to the vertebral space implant used to treat patients suffering from either diseased or damaged vertebral bodies by providing an in vivo adjustable vertebral body replacement device for use within a spinal column that eliminates torsional forces being applied at the implant vertebral body interface, maintains the desired optimized height, and offers 360 degrees of adjustment tool access for allowing lengthening and shortening of the device in vivo.

The present invention provides in one aspect, a vertebral body replacement device having a body member that includes an inner wall and an outer wall. The vertebral body replacement device also includes a central rod member that has two threaded portions; the central rod member is configured to be operatively associated within the body member. The vertebral body replacement further includes two end members with both end members being constructed to threadingly engage the two respective threaded portions of the central rod member. The body member and the two end members are constructed to inhibit rotational movement of the end members when the vertebral body replacement device is placed in a space within a spinal column. The end members will come into contact with adjacent vertebral bodies when the central rod member is rotated to cause movement of each end member in an axial direction relative to the body member, thereby causing the end members to apply a force to the two vertebral bodies to maintain the space between the vertebral bodies within the spinal column.

The present invention provides in yet another aspect, a vertebral body replacement device having an elongate body member that includes an inner wall and an outer wall with two end receptacles and a longitudinal axis extending between the two end receptacles. The vertebral body replacement device further includes a central rod member that has a first threaded portion, a second threaded portion and a central axis extending between these two portions. The central rod member is constructed to be operatively associated with the body member. The vertebral body replacement device also has a first end member and a second end member with the first end member being configured to be positioned within the first end receptacle of the body member to threadingly engage the first threaded portion of the central rod member when the central rod member is operatively associated with the body member. The vertebral body replacement device includes further a second end member that is configured to be positioned within the second end receptacle of the body member to threadingly engage the second threaded portion of the central rod member when the central rod member is operatively associated with the body member. The vertebral body replacement device has at least one footplate member that includes an end surface and a side wall, with the end surface being positioned adjacent to the side wall. The at least one footplate member is configured to detachably couple to either or both the first end member and the second end member with the end surface being sized to engage a vertebral body. The elongate body member, and first and second end members are configured to inhibit rotational movement of the first and second end members when the vertebral body replacement device is positioned within a space within a spinal column. The first and second end members will engage respective vertebral bodies when the central rod member is rotated, thereby moving the first end member and the second end member in an axial direction relative to the body member, and thus allowing the first end member and the second end member to apply a force to the two vertebral bodies.

The present invention provides in another aspect, a surgical method. The method includes the step of obtaining a vertebral body replacement device, the vertebral body replacement device has a body member, a central rod member that is configured to be operatively associated within the body member and also includes two threaded portions, and two end members that are constructed to threadingly engage the two threaded portions of the central rod member. The body member and the two end members are configured to inhibit any rotational movement of the end members when the assembled vertebral body replacement device is placed within a space between two vertebral bodies, with the two end members engaging the respective vertebral bodies following the central rod member being rotated and causing the end members to move in an axial direction relative to the body member and thus, resulting in the end members applying a force to the two vertebral bodies. The method also includes the step of positioning the vertebral body replacement device between two vertebral bodies within a patient's spinal column. The method may include the further step of operatively moving the end members in an axial direction relative to the body member to produce a force against the two vertebral bodies to maintain a space between the two vertebral bodies within the spinal column.

Further, additional features and advantages are realized through the techniques of the present invention. Other embodiments and aspects of the invention are described in detail herein and are considered a part of the claimed invention.

BRIEF DESCRIPTION OF THE DRAWINGS

The subject matter which is regarded as the invention is particularly pointed out and distinctly claimed in the claims at the conclusion of the specification. The foregoing and other objects, features and advantages of the invention are apparent from the following detailed description taken in conjunction with the accompanying drawings in which:

BEST MODE FOR CARRYING OUT THE INVENTION

Generally stated, disclosed herein is a vertebral body replacement device or vertebral spacer that typically includes a body member, a central rod member, a support ring, two end members and at least one footplate member. As used herein, the terms "vertebral body replacement device" and "vertebral spacer" may be used interchangeable as they essentially describe the same type of implant device. Further, described herein is a surgical method for using the vertebral body replacement device to maintain a space between two vertebral bodies within a patient suffering from a diseased or damaged spinal column.

Figure 1:
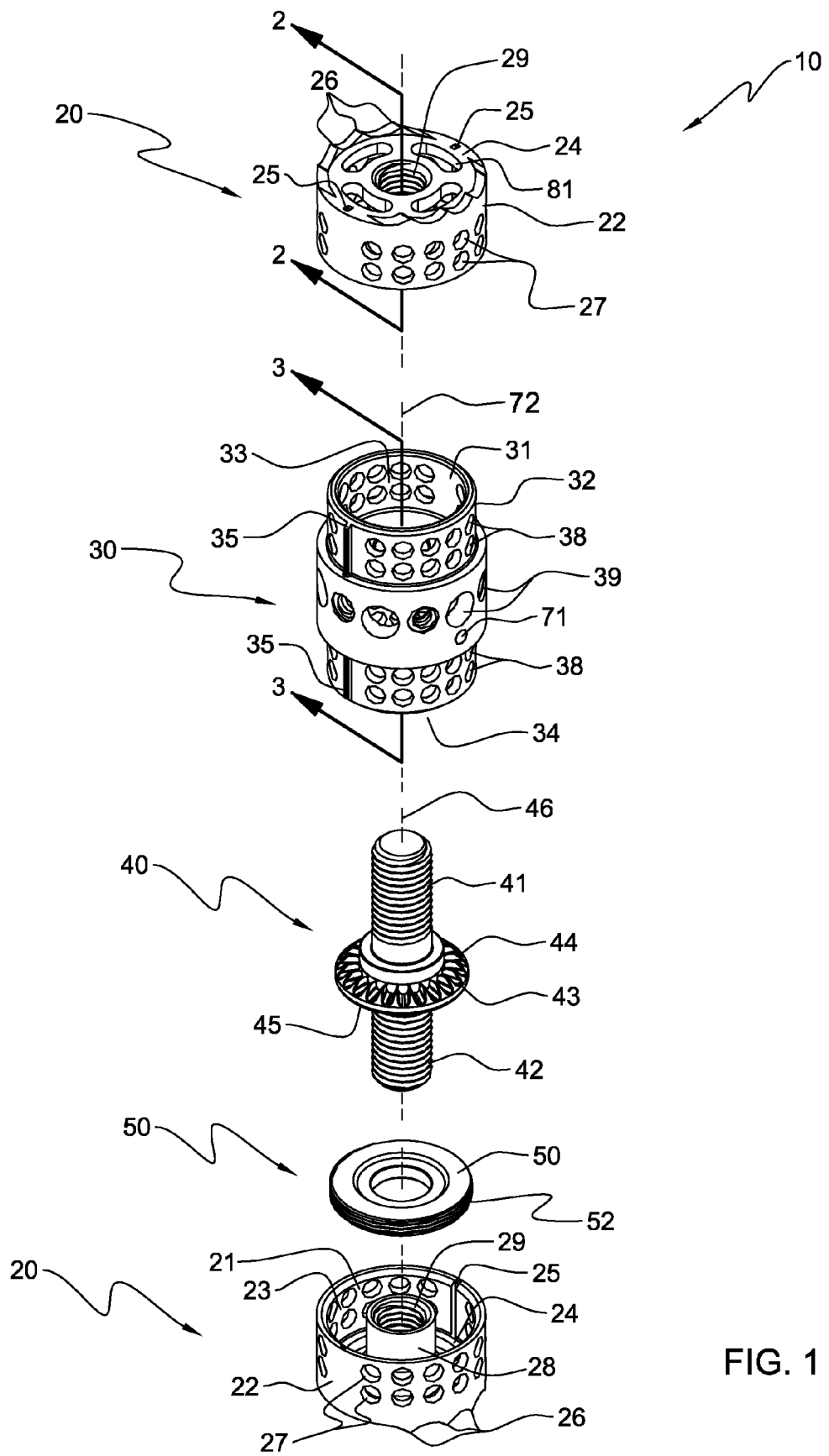
FIG. 1 is a perspective, exploded view of one embodiment of a vertebral body replacement device, in accordance with an aspect of the present invention.

As depicted in FIG. 1, the general arrangement of a vertebral body replacement device 10, in accordance with an aspect of the present invention, includes a body member 30, at least two end members 20, a central rod member 40 and a support ring 50. In this detailed description and the following claims, the words proximal, distal, anterior, posterior, medial, lateral, superior and inferior are defined by their standard usage for indicating a particular part of a bone or prosthesis according to the relative disposition of the natural bone or directional terms of reference. For example, "proximal" means the portion of a prosthesis nearest the torso, while "distal" indicates the portion of the prosthesis farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure.

With reference to FIG. 1, vertebral body replacement device 10 includes body member 30, at least two end members 20 positioned superior and inferior relative to body member 30, a central rod member 40 for placement within body member 30 and support ring 50 that is configured to contact and secure central rod member 40 within body member 30.

Exhibited in FIG. 1, body member 30 also includes an inner wall 31 and an outer wall 32, at least one hole 38 extending from outer wall 32 through inner wall 31. Further, body member 30 has at least one anti-rotational rib 35 disposed on and extending for substantially the entire length of outer wall 32. At least one rib 35 is oriented in a superior to inferior direction relative to body member 30 and substantially parallel to a longitudinal axis 72 of body member 30. At least one hole 38 is used for the placement of bone graft or other biocompatible material that will facilitate bone fusion to occur in vivo following implantation of the device. It should be understood to those skilled in the art that body member 30 may be available to the operating surgeon in various outside diameter sizes and longitudinal lengths L (see FIG. 3). Having multiple sized body members 30 as part of an implant system allows the operating surgeon to use vertebral body replacement device 10 in various levels or segments of the spine (i.e., smaller sizes in the cervical spine, medium sizes in the thoracic spine and larger sizes in the lumbar spine).

Figure 3:
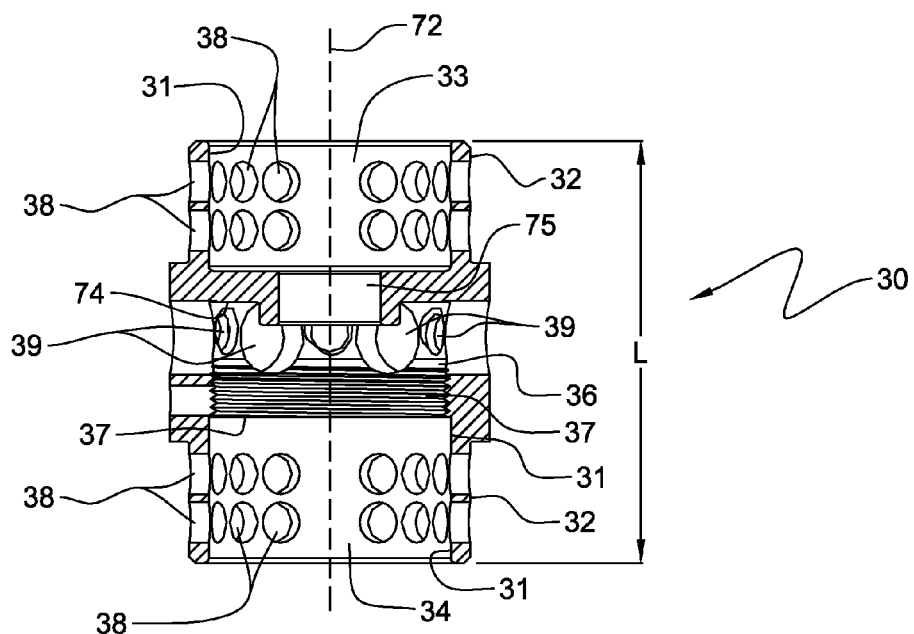
FIG. 3 is a cross-sectional, side elevational view of a body member of the vertebral body replacement device of FIG. 1 taken along line 3-3, showing two receptacle ends and internal threads for engaging a support ring, in accordance with an aspect of the present invention.

As shown in the cross-sectional view of FIG. 3, body member 30 further includes a first or superiorly positioned end receptacle 33 and a second or inferiorly positioned end receptacle 34 with longitudinal axis 72 extending between these two structures within elongate body member 30. A middle chamber 36 is defined by inner wall 31 and is bound superiorly by first end receptacle 33 and inferiorly by second end receptacle 34. At least one tool port hole 39 extends into middle chamber 36 through outer wall 32 and inner wall 31. In addition, inner wall 31 of middle chamber 36 includes a set of internal threads 37 positioned in the bottom portion of middle chamber 36. Internal threads are sized and configured to threadingly engage the external threads 52 of support ring 50 (not shown). A ceiling surface 74 bounds the superior portion of middle chamber 36 with a centralized opening 75 positioned through ceiling surface 74. Although not shown, when vertebral body replacement device 10 is fully assembled and in use, central rod member 40 is operatively associated with body member 30 by being configured to allow for a superior threaded portion 41 of central rod member 40 to pass through centralized opening 75 resulting in a collar element 47 of central rod member 40 contacting ceiling surface 74. Following placement of superior threaded portion 41 of central rod member 40 through centralized opening 75, central rod member 40 is moveably secured within middle chamber 36 by threadingly coupling support ring 50 to internal threads 37 of middle chamber 36 resulting in a bearing surface 51 of support ring 50 making pressing contact with a support surface 45 of central rod member 40. Body member 30 further includes at least one locking pin hole 71 (as seen in FIG. 1) that passes through outer wall 32 and inner wall 31 into middle chamber 36. Although not shown, following final placement and adjustment of assembled vertebral body replacement device 10, a corresponding threaded pin or bolt may screw into at least one locking pin hole 71 resulting in central rod member 40 being secured in position, fixing the overall length of vertebral body replacement 10.

Figure 4:
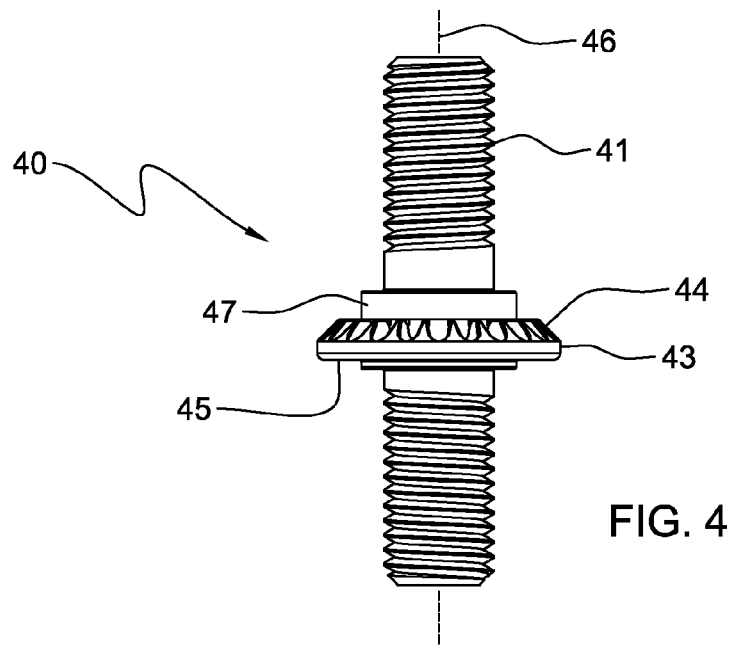
FIG. 4 is a side elevational view of a central rod member of the vertebral body replacement device of FIG. 1, in accordance with an aspect of the present invention.

FIGS. 1 and 4 show central rod member 40 having first or superior threaded portion 41 and a second or inferior threaded portion 42 with the two threaded portions having opposing thread configurations. This means that when first threaded portion 41 is constructed with right-handed threads, second threaded portion 42 is constructed with left-handed threads. It should be understood to those skilled in the art that the vice-versa thread configuration is also contemplated. Central rod member 40 further includes a central axis 46 that passes from first threaded portion 41 to second threaded portion 42 with a gear wheel portion 43 being positioned intermediate first threaded portion 41 and second threaded portion 42. Gear wheel portion 43 is generally constructed with a toothed face surface 44, the plane of toothed face surface 44 being oriented substantially perpendicular to central axis 46. Collar element 47 is positioned adjacent to tooth face surface 44 to ensure proper external access of tooth face surface 44 within middle chamber 36 following assembly of vertebral body replacement device 10. Further, gear wheel portion 43 includes support surface 45 that is located on the inferior aspect or underside of gear wheel portion 43. Similar to that described for toothed wheel surface 44, the plane of support surface 45 is correspondingly oriented substantially perpendicular to central axis 46. As explained previously, support surface 45 will contact and slidingly articulate with bearing surface 51 of support ring 50 (see FIG. 1) when vertebral body replacement device 10 is assembled and in use. Gear wheel portion 43 is integral to central rod member 40 and is positioned so that when gear wheel portion 43 is moved about its rotational axis, first threaded portion 41 and second threaded portion 42 will also rotate because gear wheel portion 43 axis of rotation is coaxial with central axis 46.

Figure 2A:
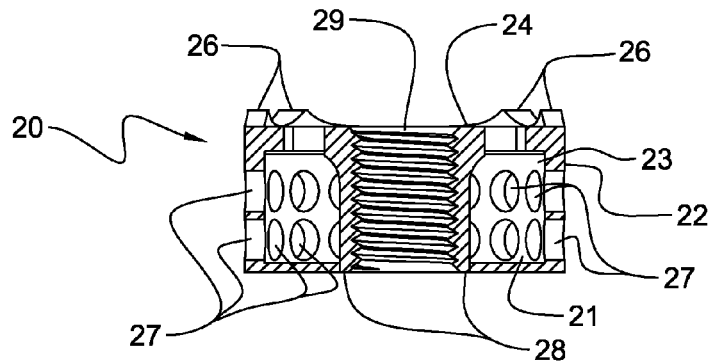
FIG. 2A is a cross-sectional, side elevational view of an end member of the vertebral body replacement device of FIG. 1 taken along line 2-2, showing an inner portion with a surrounding external wall, an internal wall and an end wall with the inner portion including a centrally oriented threaded housing element configured to engage a central rod member with the end wall being oriented normal relative to the external wall, in accordance with an aspect of the present invention.
Figure 2B:
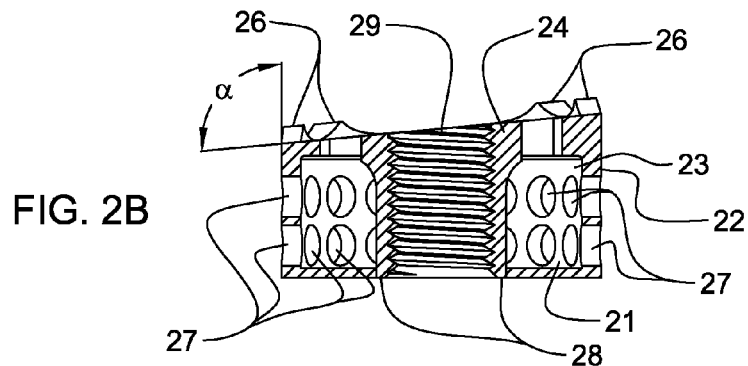
FIG. 2B is a cross-sectional, side elevational view of an alternative embodiment of an end member, showing an inner portion with a surrounding external wall, an internal wall and an end wall with the inner portion including a centrally oriented threaded housing element configured to engage a central rod member with the end wall being oriented at an angle relative to the external wall, in accordance with an aspect of the present invention.

FIGS. 1, 2A and 2B depict end member 20. Vertebral body replacement device 10 includes in its construct at least two end members 20, with the first one end member 20 being positioned superiorly relative to body member 30 and the second end member 20 being positioned inferiorly relative to body member 30. In operation, superiorly positioned first end member 20 is aligned and concentric with first end receptacle 33 so that when first end member 20 moves relative to body member 30, an internal wall 23 of end member 20 is continuously positioned adjacent to outer wall 32 of first end receptacle 33. The same operational relationship occurs with inferiorly positioned second end member 20 as it will be aligned and concentric with second end receptacle 34 so that when second end member 20 moves relative to body member 30, internal wall 23 of end member 20 is continuously positioned adjacent to outer wall 32 of second end receptacle 34.

As seen in FIGS. 2A and 2B, end member includes an inner portion 21 that is bounded by internal wall 23 and a centrally positioned threaded housing element 28. Threaded housing element 28 is constructed with internal threads 29 that may extend the full length of threaded housing element 28. Internal threads 29 are configured to correspondingly threadingly engage threaded portions 41, 42 of central rod member 40 upon assembly of vertebral body replacement device 10. Although not shown in FIGS. 2A and 2B, internal wall 23 also includes at least one channel 25 (see FIG. 1) with at least one channel 25 being oriented substantially vertical and is sized to receive corresponding at least one anti-rotational rib 35 of body member 30 when vertebral body replacement device 10 is assembled.

As further shown in the cross-sectional views of FIGS. 2A and 2B, end member 20 has an external wall 22, through which at least one hole 27 passes to adjacent internal wall 23. At least one hole 27 is sized to allow for the placement of bone graft material and other biocompatible materials for the purpose of facilitating a bone fusion bed following implantation.

Additionally, as seen in FIGS. 1 and 2A, end wall 24 functions to cap or bound inner portion 21 at one end of end member 20. End wall 24 is integrally coupled to threaded housing element 28 and generally includes at least one projection 26 or engagement element that extends in an outward direction from the outer surface of end wall 24. At least one projection 26 may be configured as a tooth-like body (as shown in FIGS. 1, 2A, 2B, and 5) although other shaped projections or engagement elements are contemplated including, but not limited to spikes, pegs, grids, fingers and posts. At least one projection 26 is sized to allow for operative engagement with the adjacent vertebral body, more specifically with the anatomic end plate of the vertebral body to provide adequate fixation post-implantation and to withstand any torsional loads that may be applied to end member 20 following implantation and during the lengthening procedure of vertebral body replacement device 10.

Cross-section view of FIG. 2A shows, end wall 24 being oriented perpendicular or normal relative to external wall 22. FIG. 2B shows an alternative embodiment of end member 20 with end wall 24 being oriented at an angle α and relative to external wall 22. Having end wall 24 being angled provides the operating surgeon with the ability to treat clinically, lordotic and kyphotic deformities. It should be well understood to those skilled in the art that end member 20 will be offered in a wide range of degrees of angulations in varying increments from 0° to 20°, thereby providing the operating surgeon with the ability to precisely treat any deformity presented during a surgical procedure.

Figure 9:
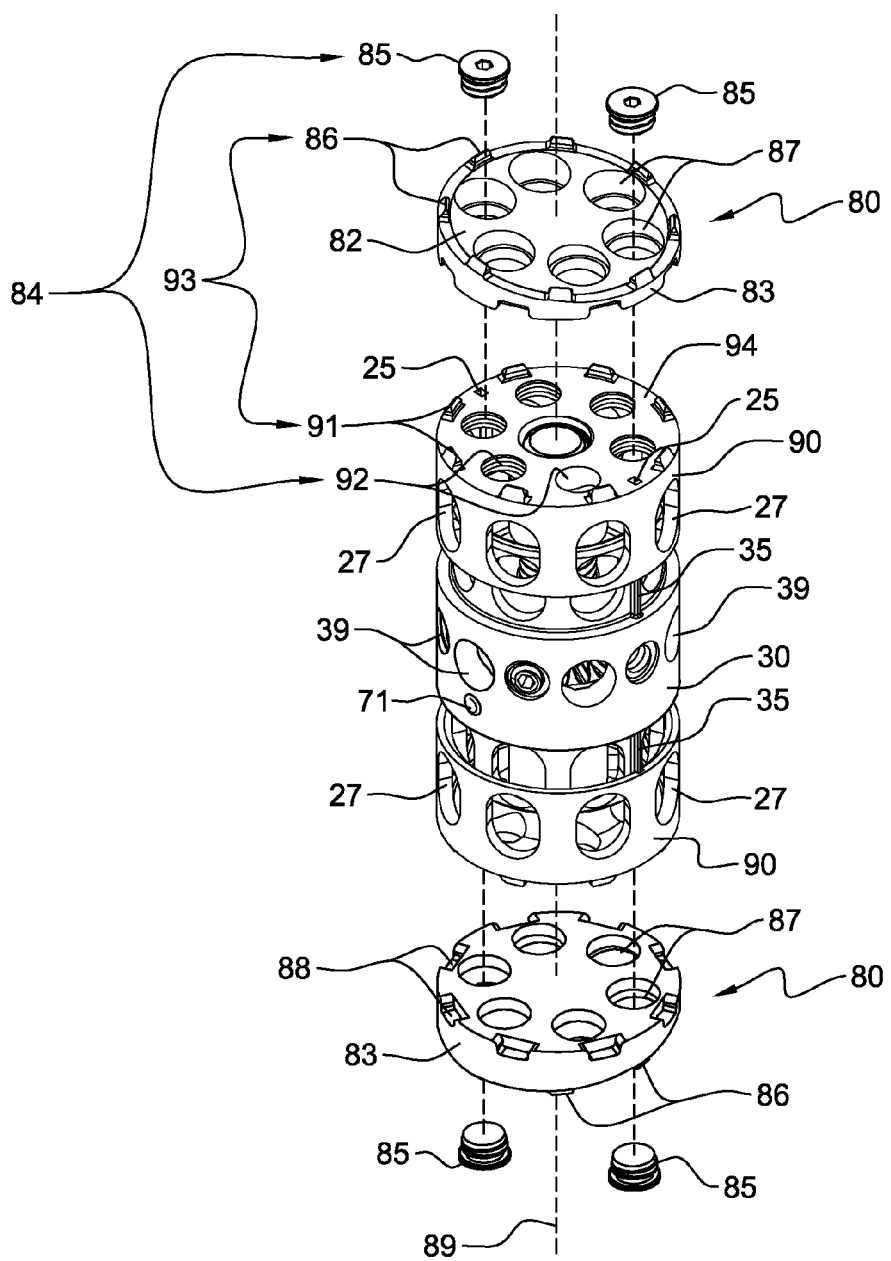
FIG. 9 is a perspective view of an alternative embodiment of a vertebral body replacement device, with a superiorly positioned, detachable footplate member and an inferiorly positioned, detachable footplate member shown prior to being coupled to the superiorly positioned end member and an inferiorly positioned end member, respectively, in accordance with an aspect of the present invention.
Figure 10A:
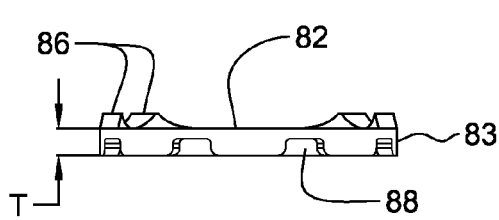
FIG. 10A is a side elevational view of a detachable footplate member used with the vertebral body replacement device of FIG. 9, showing an end surface being oriented normal relative to a sidewall, in accordance with an aspect of the present invention.
Figure 11A:
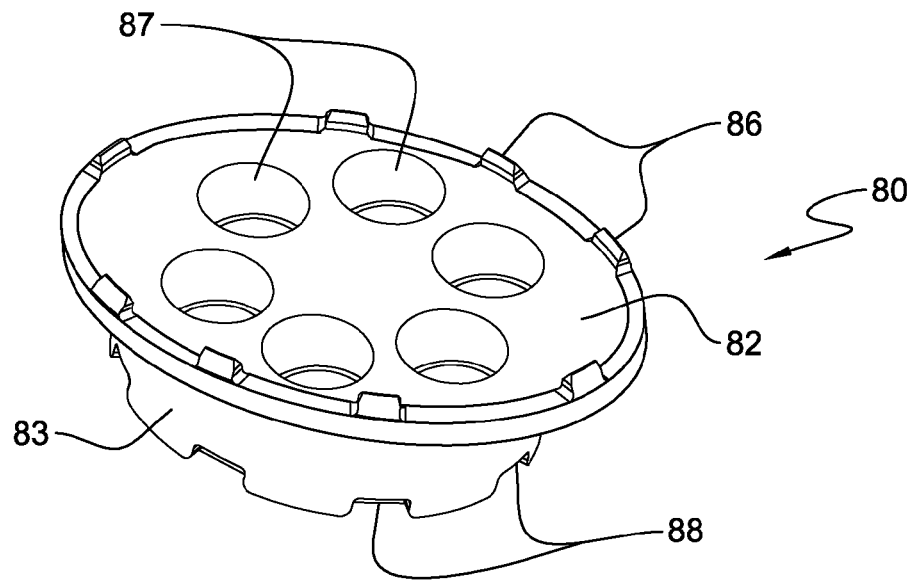
FIG. 11A is a perspective view of an alternative embodiment of a detachable foot plate member used with the vertebral body replacement device of FIG. 9, showing the end surface having an outer oval shaped profile, in accordance with an aspect of the present invention.
Figure 11B:
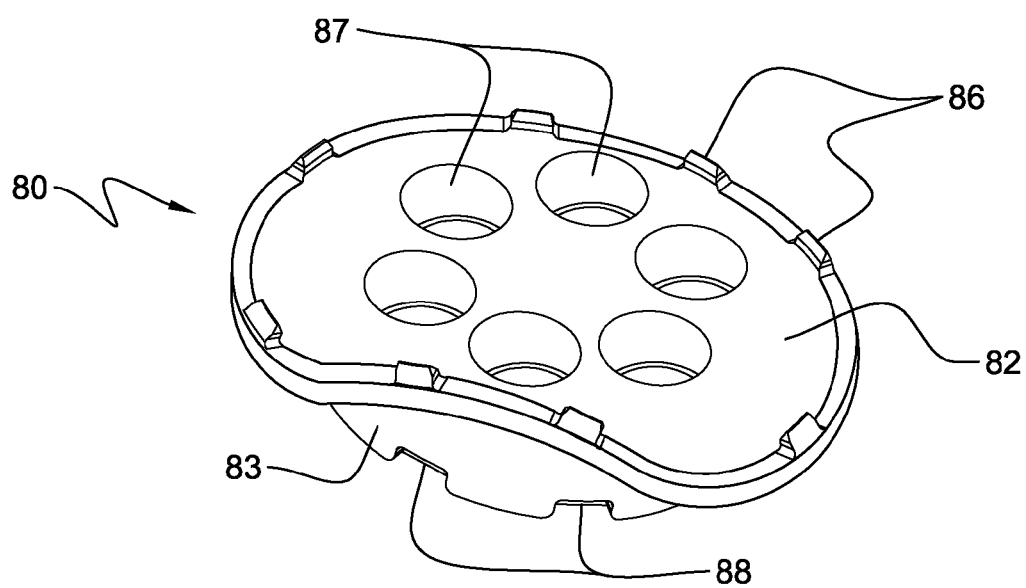
FIG. 11B is a perspective view of an alternative embodiment of a detachable footplate member used with the vertebral body replacement device of FIG. 9, showing the end surface having an outer kidney shaped profile, in accordance with an aspect of the present invention.

As shown in FIG. 9, it is contemplated that, vertebral body replacement device 10 may include an alternative embodiment of end member 90, with end wall 94 being configured to couple a footplate member 80. End wall 94 may further include at least one alignment tab 91 that functions to orient footplate member 80 in the preferred position relative to end member 90 and a vertebral body following implantation. As seen in FIGS. 11A and 11B, it is contemplated that footplate member 80 will be available in a plurality of various circular, non-circular and polygonal outer profile shapes, (i.e., circular as shown in FIG. 9, oval as shown in FIG. 11A, kidney as shown in FIG. 11B or oblong (not shown)) and sizes. It is further contemplated that footplate member 80 will be available in varying thicknesses or heights T as seen in FIG. 10A. Having a kit or implant system that includes a range of various sized heights, shapes, sizes and angled footplate members 80 provides the operating surgeon with multiple choices to maximum bone coverage, spine alignment and resulting stability of the device relative to the adjacent vertebral body following implantation.

Figure 10B:
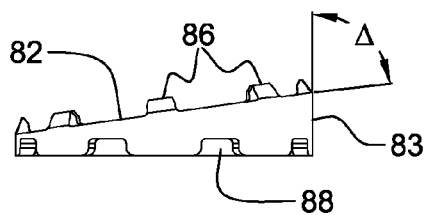
FIG. 10B is a side elevational view of an alternative embodiment of a detachable footplate member used with the vertebral body replacement device of FIG. 9, showing the end surface being oriented at an angle relative to the sidewall, in accordance with an aspect of the present invention.

As shown in FIG. 10A, an end surface 82 may be configured in a neutral or normal orientation relative to a sidewall 83 of footplate member 80. Alternatively, FIG. 10B shows footplate member 80 having end surface 82 being angled (angle Δ) relative to sidewall 83. As discussed above, it is contemplated that the operating surgeon will be provided with a plurality of footplate members 80 each having a different angle, with angulation ranging from 0° to 20°. Having such a wide range of incrementally angled footplate members 80 available will provide the operating surgeon with the ability to customize the vertebral body replacement device 10 during the operative procedure to meet the presented clinical deformity. Although shown with a circular perimeter geometry in FIG. 9, as described previously it should be understood to those skilled in the art that both neutral and angled footplate members 80 will be constructed in multiple outer profile geometric shapes, sizes and overall thickness T, again to provide the operating surgeon with the ability to maximize bone support post-implantation. Footplate member 80 may be modular in design, thereby allowing the operating surgeon to mix and match and interchange footplate members 80 with end member 90. This is accomplished by securely attaching and allowing detachment of footplate member 80 from end wall 94 of end member 90 by use of a locking mechanism 84.

For example purposes only, as shown, locking mechanism 84 may consist of at least one locking screw 85 that passes through a hole 87 in end surface 82 to engage corresponding threaded holes 92 in end wall 94. Further, it should be understood to those skilled in the art that various other low-profile locking or securement mechanisms may also be used for this purpose including, but not limited to lock pins, bolts, and press fit pins. As described above, it is contemplated that footplate member 80 will also include at least one projection 86 or engagement element that extends outwardly from the end surface 82. At least one projection 86 may be configured as a tooth-like projection (as shown in FIGS. 9, 10A, and 10B,) although other shaped engagement elements are contemplated, including but not limited to, spikes, pegs, grids, figures and posts. End surface 82 may be treated or coated with certain materials to facilitate bio-ingrowth with the adjacent vertebral body following implantation. Additionally, end surface 82 may also undergo a process or treatment that results in end surface 82 having nano-sized or micron-sized surface features. In addition, footplate member 80 may have an orientation mechanism 93 that may include alignment slots 88 that slidingly engage corresponding tabs 91 positioned around the peripheral of end member 90. Orientation mechanism 93 functions to securely orient footplate member 80 relative to end wall 94 and the adjacent vertebral body.

Figure 5:
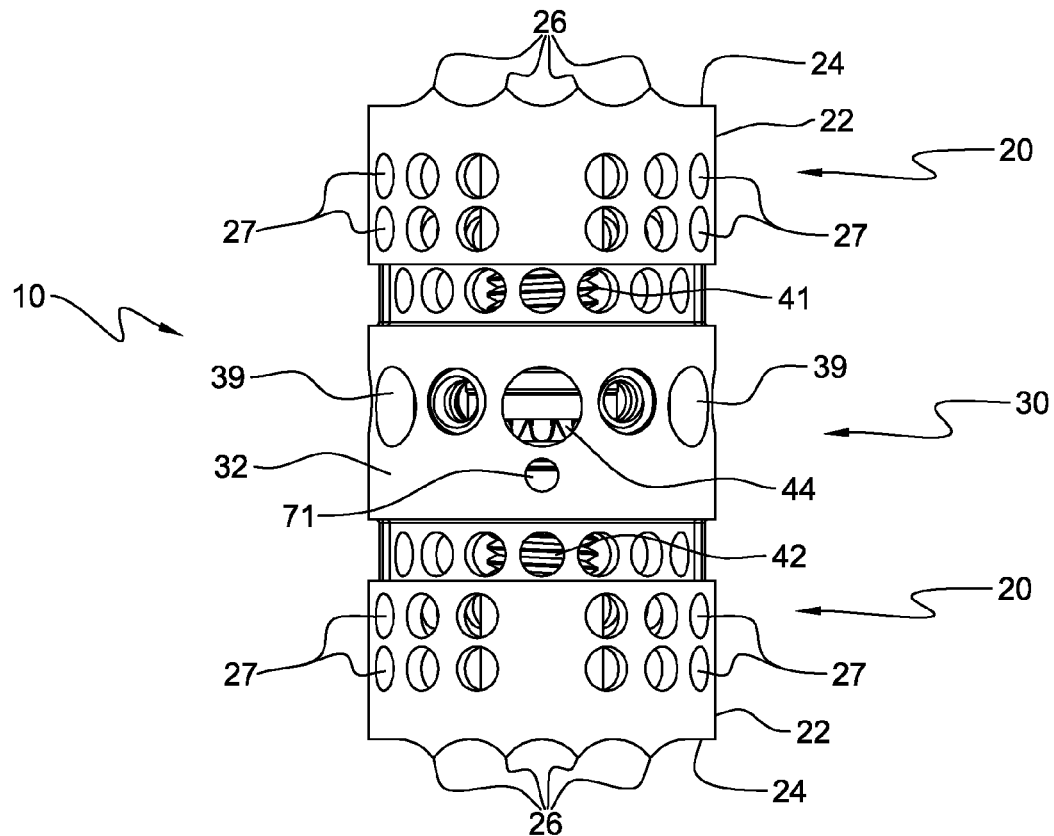
FIG. 5 is a side elevational view of the assembled vertebral body replacement device of FIG. 1, showing a superiorly positioned end member and an inferiorly positioned end member extended away from the body member, in accordance with an aspect of the present invention.
Figure 6:
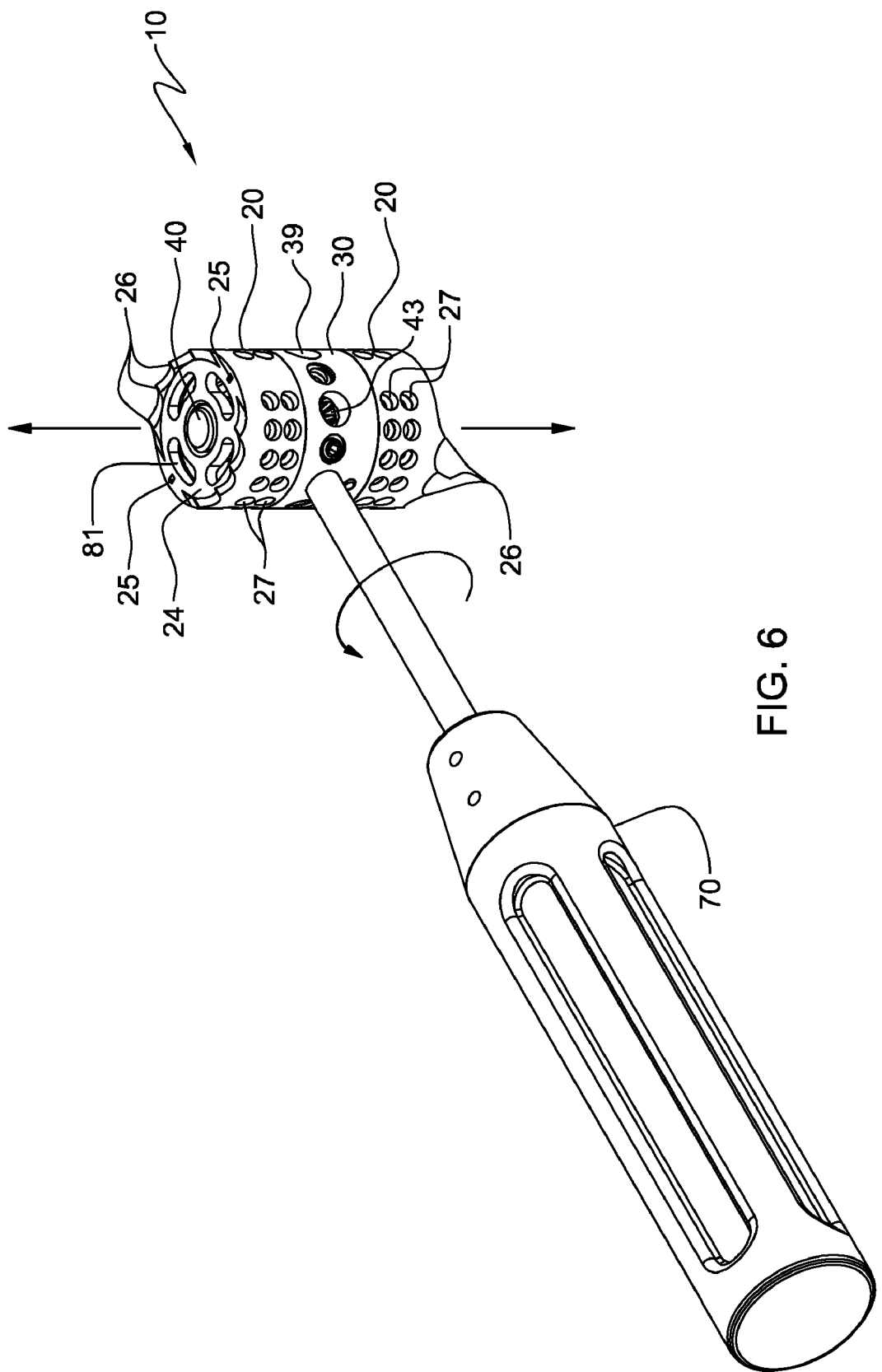
FIG. 6 is a perspective view of the vertebral body replacement device of FIG. 1, with a tool inserted through a tool port hole and in operable position with the central rod member, in accordance with an aspect of the present invention.

Following the assembly of vertebral body replacement device 10, superiorly positioned or first end member 20 and inferiorly positioned or second end member 20 are both positioned with each respective inner portion 21 and threaded housing element 28 within first end receptacle 33 and second end receptacle 34, respectively. As shown in FIG. 6, first end member 20 and second end member 20 may be simultaneously extended or retracted in an axial direction relative to body member 30 resulting in either the lengthening or shortening of the over-all length of vertebral body replacement device 10 by inserting a tool 70 through tool port hole 39 to engage the gear shaped tip (not shown) of tool 70 with tooth faced surface 44 of gear wheel portion 43 of central rod member 40. In operation, tool 70 is rotated causing gear wheel portion 43 to rotate resulting in first and second threaded portions 41, 42 rotating about central axis 46. When assembled, threaded housing element 28 of first and second end members 20 are threaded onto first and second threaded portions 41, 42 of central rod member 40 respectively, with at least one channel 25 of first and second end members 20 also engaging at least one anti-rotational rib 35 positioned on outer wall 32 of first and second end receptacles 33, 34, respectively. Functionally, the engagement of at least one channel 25 of first and second end members 20 with at least one rib 35 of body member 30 prohibits rotational movement of the first and second end members 20 when tool 70 is turned, thus resulting in first and second end members 20 simultaneously advancing or moving in opposing axial directions relative to body member 30 for a maximum distance equal to the thread length of first and second thread portions 41, 42 of central rod member 40. As discussed above, the bi-directional axial motion of the first end and second end members 20 is caused by the opposing threads (i.e., right-handed and left handed threads) of the respective first and second threaded portion 41, 42 of the central rod member 40. Operationally, central rod member 40 converts the rotational motion of tool 70 and gear wheel portion 43 into corresponding axial or linear movement of first and second end members 20, with the mating of channel 25 and rib 35 substantially prohibiting any rotational movement of two end members 20 relative to longitudinal axis 72 and the adjacent vertebrae, thus eliminating torsional forces being applied to the end member-vertebral body interface. For example purposes, FIG. 5 shows an assembled vertebral body replacement device 10 following partial simultaneous movement of first and second end members 20 as describe above.

Figure 8:
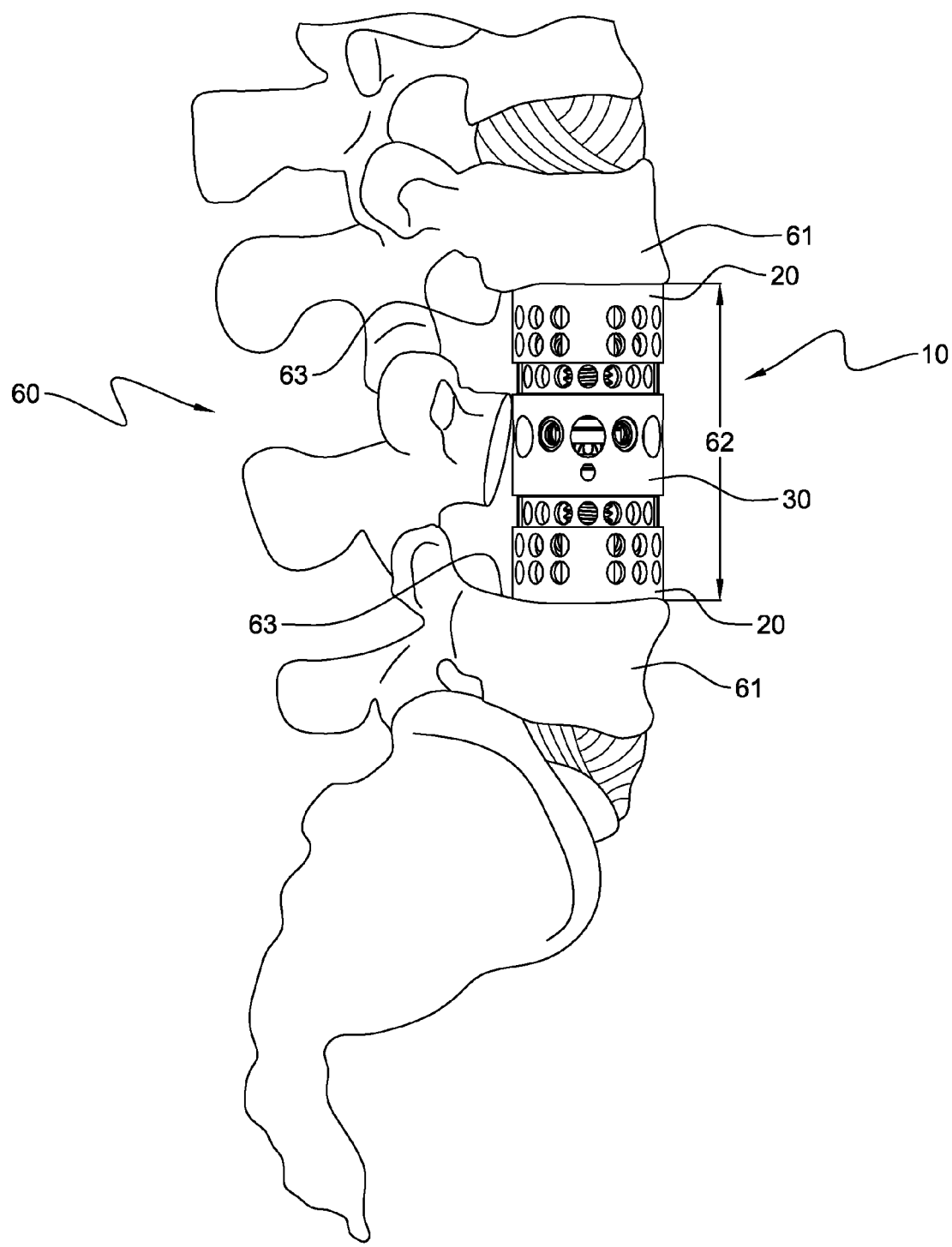
FIG. 8 is a side elevational view of the vertebral body replacement device of FIG. 1, shown positioned between two vertebral bodies with the superiorly positioned end member and the inferiorly positioned end member extended to maintain a desired space within a spinal column, in accordance with an aspect of the present invention.

FIG. 8 shows assembled vertebral body replacement device 10 positioned within a space between two vertebral bodies following simultaneous movement of first and second end members 20 in the manner described above, resulting in intimate contact between an adjacent vertebral body and at least one projection 26 extending from end wall 24, or alternatively, projection 86 of footplate member 80 (not shown). A resultant compressive force is applied by each end member 20 (or footplate member 80) against the contacted vertebral body to maintain the desired anatomic spacing.

The surgical technique for implantation of a vertebral body replacement device is well known in the art, including the appropriate surgical exposure and dissection techniques. The method includes, obtaining a vertebral body replacement device 10 that may include body member 30, central rod member 40 that has two threaded portions 41, 42 and is configured to be operatively associated within body member 30 and first and second end members 20 that are configured to threadingly engage the two threaded portions 41, 42 of central rod member 40. As discussed above, body member 30 and end members 20 are further configured to inhibit rotational movement of two end members 20 following assembly and positioning of vertebral body replacement device 10 within a space within a spinal column with both end members 20 engaging respective vertebral bodies when central rod member 40 is rotationally actuated, thus causing two end members 20 to move in opposing axial directions relative to body member 30. Upon such movement, two end members 20 will apply a force to the two adjacent vertebral bodies within the spinal column. It should be understood that all of the above noted device components and respective elements include the same structural and functionality characteristics as described previously herein.

Figure 7:
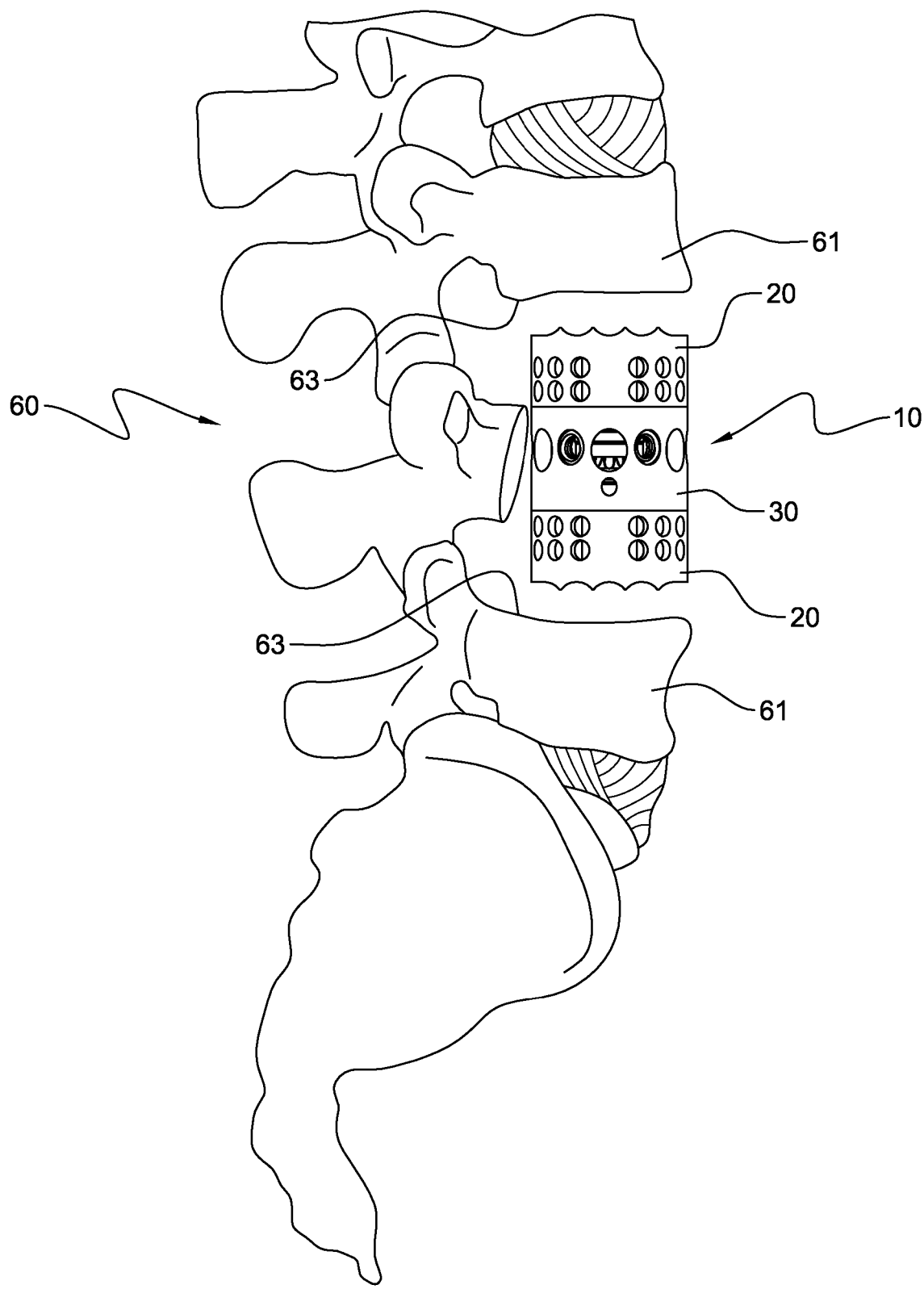
FIG. 7 is a side elevational view of the vertebral body replacement device of FIG. 1, shown disposed within a space between two vertebral bodies within a spinal column prior to the translational movement of the superiorly positioned end member and the inferiorly positioned end member, in accordance with an aspect of the present invention.

As seen in FIG. 7, the method may further include the step of positioning vertebral body replacement device 10 between two vertebral bodies within a patient's spinal column. The surgical method may also include the step of simultaneously operatively moving in opposing directions both end members 20 relative to body member 30 to produce a force against the two respective adjacent vertebral bodies for the purpose of maintaining a space between the two vertebral bodies within the spinal column as shown in FIG. 8. Although not shown, the method may further include the step of engaging tool 70 with central rod member 40 through tool portal hole 39, whereby rotary motion of tool 70 is converted into opposing axial movement of two respective end members 20 relative to body member 30 causing two end members 20 to come in contact and apply a force to the adjacent vertebral bodies, thereby maintaining the space between these two vertebral bodies. The method also may include the step of securely coupling to body member 30 a lock pin through lock pin hole 71 following finalization of the length adjustment procedure to ensure securement of two end members 20 relative to body member 30 and central rod member 40.

It should be understood by those skilled in the art that the surgical method described herein may also include alternatively, using the modular footplate member 80 that has been coupled to alternative embodiment end member 90 which has been more fully described above. The sequence of implantation of vertebral body replacement device 10 as described herein may be different depending upon the given clinical situation and whether footplate members 80 are attached on the "back table" prior to the complete assembly of vertebral body replacement device 10 or within the operative site. The sequence of device assembly will be at the discretion of the operating surgeon and will vary depending upon the preference of the operating surgeon in combination with the clinical needs of the patient.

It is further contemplated that an implant system comprised of various cross-sectional sizes, cross-sectional polygonal and circular/oval shapes and longitudinal lengths of body members 30, end members and footplate member 80 will be available as a kit. This will allow the operating surgeon to pick and choose the separate member components to assemble vertebral body replacement device 10 that best fits into a certain spinal segment or to address an anatomical deformity presented in a patient. It should be understood by those skilled in the art that each shaped and dimensioned member provided will function in the same manner as described previously herein with central rod member 40 and supporting ring 50.

Although the preferred embodiments have been depicted and described in detail herein, it will be apparent to those skilled in the relevant art that various modifications, additions and substitutions can be made without departing from its essence and therefore these are to be considered to be within the scope of the following claims.

What is claimed is:

1. A vertebral body replacement device comprising: a body member having an inner wall, an outer wall, and a Longitudinal axis, the body member having at least one tool port extending from the outer wall through the inner wall and toward the Longitudinal axis of the body member; a central rod member having a first threaded portion and a second threaded portion, the central rod member being configured to be operatively associated within the body member, the central rod member comprising a gear wheel portion, the gear wheel portion having a toothed surface and a support surface, the toothed surface exposed through the at least one tool port when the central rod member is operatively associated within the body member; a first end member and a second end member, the first end member being configured to threadingly engage the first threaded portion of the central rod member and the second end member being configured to threadingly engage the second threaded portion of the central rod member; and wherein the body member, and first and second end members are configured to inhibit rotational movement of the first and second end members when the vertebral body replacement device is disposed within a space within a spinal column with the first and second end members engaging respective vertebral bodies of the spinal column and the central rod member is rotationally actuated to move the first end member and the second end member in an axial direction relative to the body member allowing for the first end member and the second end member to apply a force to the two vertebral bodies to maintain a desired space therebetween, wherein the at least one tool port comprises a plurality of tool ports positioned in a circular arrangement around a perimeter of the body member, each tool port extending from the outer wall through the inner wall and toward the longitudinal axis of the body member, the toothed surface of the gear wheel portion exposed through the plurality of tool ports when the central rod member is operatively associated within the body member.

2. The vertebral body replacement device of claim 1, wherein the body member is an elongate body comprising a first end receptacle and a second end receptacle, the longitudinal axis extending between the first end receptacle and the second end receptacle thereof.

3. The vertebral body replacement device of claim 1, wherein the first end member and the second end member each further comprise an external wall, an internal wall and an end wall, wherein each of the first end member and the second end member have at least one channel extending from the end wall.

4. The vertebral body replacement device of claim 3, wherein for at least one of the first end member and the second end member at least one projection is disposed on the end wall and extends in an outward direction from each end wall to engage the respective two vertebral bodies when the vertebral body replacement device is in use within the spinal column.

5. The vertebral body replacement device of claim 3, wherein for at least one of the first end member and the second end member, the end wall is disposed at an angle relative to the external wall.

6. The vertebral body replacement device of claim 3, wherein for each of the first end member and the second end member, the first end member and the second end member further comprise at least one hole disposed in at least one of the external wall and the end wall and extending therethrough, thereby allowing for the placement of bio-compatible material within the first and second end members.

7. The vertebral body replacement device of claim 1, further comprising a support ring, the support ring having a bearing surface, contacting the central rod member when the central rod member is operatively positioned within the body member.

8. The vertebral body replacement device of claim 7, the support surface of the gear wheel portion being configured to contact the bearing surface of the support ring when the central rod member is operatively positioned within the body member.

9. The vertebral body replacement device of claim 1, wherein the central rod member further comprises a central axis extending between the first threaded portion and the second threaded portion thereof, and wherein the rotational axis of the gear wheel portion is substantially coaxial to the central axis of the central rod member, thereby when the gear wheel portion is rotated about the rotational axis the first and second threaded portions correspondingly rotate about the central axis of the central rod member.

10. The vertebral body replacement device of claim 1, further comprising at least one footplate member, wherein the at least one footplate member couples to at least one of the first end member and the second end member.

11. The vertebral body replacement device of claim 1, the body member further comprising at least one hole extending from the outer wall through the inner wall therethrough, thereby allowing for the placement of bio-compatible material within the body member.

12. A vertebral body replacement device comprising: a body member, wherein the body member is an elongate body having an inner wall and an outer wall, and comprising a first end receptacle, a second end receptacle and a longitudinal axis extending between the first end receptacle and the second end receptacle thereof, the body member having at least one tool port extending from the outer wall through the inner wall and toward the longitudinal axis of the body member; a central rod member having a first threaded portion, a second threaded portion and a central axis extending therebetween, the central rod member being configured to be operatively associated with the body member, the central rod member comprising a gear wheel portion, the gear wheel portion having a toothed surface and a support surface; a first end member and a second end member, wherein the first end member is configured to be positioned within the first end receptacle of the body member to threadingly engage the first threaded portion of the central rod member when the central rod member is operatively associated with the body member, and the second end member is configured to be positioned within the second end receptacle of the body member to threadingly engage the second threaded portion of the central rod member when the central rod member is operatively associated with the body member; at least one footplate member, wherein the at least one footplate member includes an end surface and a sidewall, the end surface being positioned adjacent to the sidewall, and wherein the at least one footplate couples to at least one of the first end member and the second end member with the end surface being sized and configured to engage a vertebral body; and wherein the body member, and first and second end members are configured to inhibit rotational movement of the first and second end members when the vertebral body replacement device is disposed within a space within a spinal column with the first and second end members engaging respective vertebral bodies of the spinal column and the central rod member is rotationally actuated to move the first end member and the second end member in an axial direction relative to the body member allowing for the first end member and the second end member to apply a force to the two vertebral bodies, wherein the at least one tool port comprises a plurality of tool ports positioned in a circular arrangement around a perimeter of the body member, each tool port extending from the outer wall through the inner wall and toward the longitudinal axis of the body member, the toothed surface of the gear wheel portion exposed through the plurality of tool ports when the central rod member is operatively associated within the body member.

13. The vertebral body replacement device of claim 12, wherein the first end member and the second end member each further comprise an inner portion being bounded by an external wall, an internal wall and an end wall, wherein each of the first end member and the second end member have at least one channel extending from the end wall.

14. The vertebral body replacement device of claim 13, wherein for each of the first end member and the second end member, the first end member and the second end member further comprise at least one hole disposed in the external wall and extending therethrough, thereby allowing for the placement of bio-compatible material within the inner portion of the first and second end members.

15. The vertebral body replacement device of claim 12, further comprising a support ring, the support ring having a bearing surface contacting the central rod member when the central rod member is operatively positioned within the body member.

16. The vertebral body replacement device of claim 15, the support surface of the gear wheel portion being configured to contact the bearing surface of the support ring when the central rod member is operatively positioned within the body member.

17. The vertebral body replacement device of claim 16, wherein the central rod member further comprises a central axis extending between the first threaded portion and the second threaded portion thereof, and wherein the rotational axis of the gear wheel portion is substantially coaxial to the central axis of the central rod member, thereby when the gear wheel portion is rotated about the rotational axis the first and second threaded portions correspondingly rotate about the central axis of the central rod member.

18. The vertebral body replacement device of claim 12, wherein for the at least one footplate member at least one projection is disposed on the end surface and extends in an outward direction from the end surface to engage the respective two vertebral bodies when the vertebral body replacement device is in use within the spinal column.

19. The vertebral body replacement device of claim 12, wherein for the at least one footplate, the end surface is disposed at an angle relative to the side wall.

20. The vertebral body replacement device of claim 12, the body member further comprising at least one hole extending from the outer wall through the inner wall therethrough, thereby allowing for the placement of bio-compatible material within the body member.

* * * * *